United States Patent [19]

Kaplan et al.

[11] Patent Number: 5,475,063
[45] Date of Patent: Dec. 12, 1995

[54] BLENDS OF GLYCOLIDE AND/OR LACTIDE POLYMERS AND CAPROLACTONE AND/OR TRIMETHYLENE CARBONATE POLYMERS AND ABSORBABLE SURGICAL DEVICES MADE

[75] Inventors: Donald S. Kaplan, Weston, Conn.; Matthew Hermes, Steamboat Springs, Colo.; Ross R. Muth, Brookfield; John Kennedy, Stratford, both of Conn.

[73] Assignee: United States Surgical Corporation, Norwalk, Conn.

[21] Appl. No.: 356,030

[22] Filed: Dec. 14, 1994

Related U.S. Application Data

[60] Continuation of Ser. No. 184,091, Jan. 19, 1994, abandoned, which is a division of Ser. No. 45,898, Apr. 12, 1993, Pat. No. 5,320,624, which is a continuation-in-part of Ser. No. 768,168, Sep. 30, 1991, abandoned, which is a continuation-in-part of Ser. No. 654,234, Feb. 12, 1991, abandoned.

[51] Int. Cl.$^6$ .......................... C08L 67/04; C08L 69/00; C08G 63/08
[52] U.S. Cl. ...................... 525/411; 525/413; 525/415
[58] Field of Search ......................... 525/411, 413, 525/415

[56] References Cited

U.S. PATENT DOCUMENTS

| | | |
|---|---|---|
| 2,668,136 | 2/1954 | Winkler. |
| 2,668,162 | 7/1954 | Lowe. |
| 2,683,136 | 7/1954 | Higgins. |
| 2,703,316 | 3/1955 | Schneider. |
| 2,758,987 | 8/1956 | Salzberg. |
| 3,225,766 | 12/1965 | Baptist et al.. |
| 3,268,486 | 8/1966 | Klootwijk. |
| 3,268,487 | 8/1966 | Klootwijk. |
| 3,297,033 | 1/1967 | Schmitt et al.. |
| 3,422,181 | 1/1969 | Chirgwin, Jr.. |
| 3,442,871 | 5/1969 | Schmitt et al.. |
| 3,463,158 | 8/1969 | Schmitt et al.. |
| 3,468,853 | 9/1963 | Schmitt et al.. |
| 3,531,561 | 9/1970 | Trehu. |
| 3,565,869 | 2/1971 | DeProspero. |
| 3,597,449 | 8/1971 | DeProspero et al.. |
| 3,620,218 | 11/1971 | Schmitt et al.. |
| 3,626,948 | 12/1971 | Glick et al.. |
| 3,636,956 | 1/1972 | Schneider. |
| 3,736,646 | 6/1973 | Schmitt et al.. |
| 3,739,773 | 6/1973 | Schmitt et al.. |
| 3,772,420 | 11/1973 | Glick et al.. |
| 3,773,919 | 11/1973 | Boswell et al.. |
| 3,781,349 | 12/1973 | Ramsey et al.. |
| 3,784,585 | 1/1974 | Schmitt et al.. |
| 3,792,010 | 2/1974 | Wasserman et al.. |
| 3,797,499 | 3/1974 | Schneider. |
| 3,839,297 | 10/1974 | Wasserman et al.. |
| 3,846,382 | 11/1974 | Ramsey et al.. |
| 3,867,190 | 2/1975 | Schmidt et al.. |
| 3,875,937 | 4/1975 | Schmitt et al.. |
| 3,878,284 | 4/1975 | Schmitt et al.. |
| 3,896,802 | 7/1975 | Williams. |
| 3,902,497 | 9/1975 | Casey. |
| 3,937,223 | 2/1976 | Roth. |
| 3,982,543 | 9/1976 | Schmitt et al.. |
| 4,033,938 | 7/1977 | Augurt et al.. |
| 4,045,418 | 8/1977 | Sinclair. |
| 4,057,537 | 11/1977 | Sinclair. |
| 4,060,089 | 11/1977 | Noiles. |
| 4,137,921 | 2/1979 | Okuzumi et al.. |
| 4,157,437 | 6/1979 | Okuzumi et al.. |
| 4,201,216 | 5/1980 | Mattei. |
| 4,243,775 | 1/1981 | Rosensaft et al.. |
| 4,246,904 | 1/1981 | Kaplan. |
| 4,273,920 | 6/1981 | Nevin. |
| 4,275,813 | 6/1981 | Noiles. |
| 4,279,249 | 7/1981 | Vert et al.. |
| 4,300,565 | 11/1981 | Rosensaft ............................ 525/415 |
| 4,343,931 | 8/1982 | Barrows. |
| 4,402,445 | 9/1983 | Green. |
| 4,429,080 | 1/1984 | Casey et al.. |
| 4,539,981 | 9/1985 | Tunc. |
| 4,550,449 | 11/1985 | Tunc. |
| 4,595,713 | 5/1986 | St. John. |
| 4,605,730 | 6/1986 | Shalaby et al.. |
| 4,620,541 | 11/1986 | Gertzman et al.. |
| 4,624,256 | 11/1986 | Messier et al.. |
| 4,643,734 | 2/1987 | Lin. |
| 4,655,777 | 4/1987 | Dunn et al.. |
| 4,700,704 | 10/1987 | Jamiolkowski et al.. |
| 4,741,337 | 3/1988 | Smith et al.. |
| 4,744,365 | 5/1988 | Kaplan et al.. |
| 4,889,119 | 12/1989 | Jamiolkowski et al.. |
| 4,891,263 | 1/1990 | Kotliar et al.. |
| 4,905,680 | 3/1990 | Tunc. |

(List continued on next page.)

FOREIGN PATENT DOCUMENTS

| | | |
|---|---|---|
| 779291 | 7/1957 | United Kingdom. |
| 1034123 | 6/1966 | United Kingdom. |
| 1332505 | 10/1973 | United Kingdom. |
| 1414600 | 11/1975 | United Kingdom. |
| 2033411 | 5/1980 | United Kingdom. |
| 2102827 | 2/1983 | United Kingdom. |

OTHER PUBLICATIONS

Kulkarni, et al., J. Biomed. Mater, Res., 1971, 5, pp. 169–181.

Vert, et al., Makromol. Chem., Suppl., 1981, 5,30–41.

D. K. Gilding et al. "Biodegradable polymers for use in surgery–polyglycolic/poly(actic acid) homo–and copolymers: 1", Polymer, vol. 20, pp. 1459–1464 (1979).

D. F. Williams (ed) Biocompatibility of Clinical Implant Materials, vol. II Chapter 9: "Biodegradable Polymers" (1981).

*Primary Examiner*—David Buttner

[57] ABSTRACT

Polymer blends of glycolide and/or lactide homopolymer and/or glycolide/lactide copolymer and polycaprolactone and/or polytrimethylene carbonate homopolymer or copolymers thereof and absorbable surgical devices manufactured therefrom having improved mechanical properties, such as improved impact resistance and improved cyclic flex, are disclosed. The blends may be prepared by polymerizing a glycolide or lactide containing polymer in the presence of a polymer derived from trimethylene carbonate or ε-caprolactone.

20 Claims, No Drawings

U.S. PATENT DOCUMENTS

| | | |
|---|---|---|
| 4,916,193 | 4/1990 | Tang et al. . |
| 4,920,203 | 4/1990 | Lang et al. . |
| 4,965,300 | 10/1990 | Eichenauer et al. . |
| 4,994,074 | 2/1991 | Bezwada et al. . |
| 5,037,950 | 8/1991 | Bezwada et al. . |
| 5,047,048 | 9/1991 | Bezwada et al. . |
| 5,061,281 | 10/1991 | Mares et al. . |
| 5,066,772 | 11/1991 | Tang et al. . |
| 5,080,665 | 1/1992 | Jarrett ............ 525/415 |
| 5,120,802 | 6/1992 | Mares et al. . |
| 5,145,945 | 4/1992 | Tang et al. . |
| 5,152,781 | 10/1992 | Tang et al. . |
| 5,185,408 | 2/1993 | Tang et al. . |

BLENDS OF GLYCOLIDE AND/OR LACTIDE POLYMERS AND CAPROLACTONE AND/OR TRIMETHYLENE CARBONATE POLYMERS AND ABSORBABLE SURGICAL DEVICES MADE

CROSS REFERENCE TO RELATED APPLICATION

This application is a continuation of U.S. application Ser. No. 08/184,091, (now abandoned) filed on Jan. 19, 1994 which is divisional of U.S. application Ser. No. 08/045,898 (U.S. Pat. No. 5,320,624) filed on Apr. 12, 1993 which is a continuation-in-part of U.S. application Ser. No. 07/768,168 (now abandoned) filed on Sep. 30, 1991 which is a continuation in part of U.S. application Ser. No. 07/654,234 (now abandoned) filed on Feb. 12, 1991.

BACKGROUND OF THE INVENTION

This invention relates to glycolide and/or lactide based polymer compositions and more particularly to polymer compositions which are blends of a glycolide and/or lactide homopolymer or glycolide/lactide copolymer and polycaprolactone homopolymer and/or polytrimethylene carbonate homopolymer and/or caprolactone or trimethylene carbonate copolymer, said polymer compositions being particularly useful in the manufacture of absorbable surgical devices.

Polymers and copolymers of, and surgical devices made from, lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,773,919, 3,781,349, 3,784,585, 3,792,010, 3,797,499, 3,839,297, 3,846,382, 3,867,190, 3,875,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600, and 2,102,827, D. K. Gilding et al., "Biodegradable polymers for use in surgery-polyglycolic/poly (lactic acid) homo- and copolymers: 1," *Polymer,* Volume 20, pages 1459–1464 (1979), and D. F. Williams (ed.), *Biocompatibility of Clinical Implant Materials,* Volume II, chapter 9: "Biodegradable Polymers" (1981). All of the foregoing documents are hereby incorporated by reference. Some of the foregoing documents listed mention or discuss annealing, heat-treating, or post-treating surgical articles containing the lactide/glycolide/related compound polymers or copolymers. See, e.g., U.S. Pat. Nos. 3,422,181, 3,626,948, 3,636,956, 3,772,420, 3,792,010, 3,797,499, 3,839,297, 3,878,284, 4,137,921, 4,157,437, 4,243,775, 4,300,565, U.K. Pat. or Appln. Nos. 1,332,505, 1,414,600, and 2,102, 827, and U.S. Pat. Nos. 4,137,921, 4,157,437, 4,243,775, and 4,300,565.

In U.S. Pat. No. 4,744,365 it was found that certain two-phase compositions derived from lactide and glycolide in which lactide moieties predominate, have a remarkable and unexpected balance of desirable properties. Those properties include lack of brittleness and the ability to be injection molded and annealed. The properties of the composition make it possible to injection mold surgical devices (e.g., staples, clips) from the composition and to anneal those devices to obtain devices having a remarkable and unexpected balance of desirable properties. As compared to a substantially amorphous, one-phase poly(lactide/glycolide) device of a given composition, the annealed, two-phase device of the same overall composition has a much higher distortion temperature but essentially the same in vivo rate of loss of tensile strength. Thus, the compositions of U.S. Pat. No. 4,744,365 make it possible to increase the resistance to thermal distortion of poly(lactide/glycolide) surgical devices without adversely affecting their rate of loss of tensile strength. More particularly, the compositions of U.S. Pat. No. 4,744,365 comprise a multi-phase polymeric composition derived from lactide and glycolide, the first phase having about 0 to about 25% m glycolide moieties and about 75 to about 100% m lactide moieties and the other phases having glycolide and lactide moieties in amounts such that the composition overall has up to 45% m glycolide moieties, wherein the first phase constitutes at least 50% (and preferably not more than about 95%) by weight of the composition.

In addition to the afore-recited patents and other documents which disclose polymers and copolymers of, and surgical devices made from lactide and glycolide, other patents disclose surgical devices prepared from copolymers of lactide or glycolide and other monomers including caprolactone or trimethylene carbonate. Such patents include U.S. Pat. Nos. 4,700,704, 4,605,730 and 4,643,734. More particularly, U.S. Pat. Nos. 4,605,730 and 4,700,704 disclose copolymers of epsilon-caprolactone and glycolide useful in making surgical articles and particularly surgical sutures having low Young's modulus. In addition to the afore-recited patents, U.S. Pat. No. 4,624,256 discloses the utilization of high molecular weight caprolactone polymers as coatings for surgical sutures, while U.S. Pat. No. 4,429,080 discloses surgical articles manufactured from triblock copolymers prepared from copolymerizing glycolide with trimethylene carbonate.

U.S. Pat. No. 5,080,665 describes a surgical composite structure including a plurality of fibers as a reinforcing component and a matrix of a deformable at ambient temperature bioabsorbable component comprising a blend of a first and second absorbable polymer, the first absorbable polymer comprising a plurality of linkages selected from the group consisting of glycolic acid ester and lactic acid ester linkages and mixtures thereof and the second absorbable polymer comprising a plurality of linkages selected from the group consisting of 1,3-dioxan-2-one; 1,4-dioxan-2-one and ε-caprolactone linkages, the first absorbable polymer comprising at least about 50 up to about 90 weight percent of the blend. Materials listed as suitable for the second absorbable polymer are: 1) poly(trimethylene carbonate); 2) poly(p-dioxanone); 3) poly(E-caprolactone); 4) copolymers of poly(trimethylene carbonate), poly(p-dioxanone) or poly(E-caprolactone); and 5) other polymers or copolymers with glass transition temperatures below room temperature. No mention is made of a blend which includes either a lactide/trimethylene carbonate copolymer or a blend including lactide/trimethylene carbonate copolymer having a trimethylene carbonate content of at least about 70%, or forming fibers from such blends.

SUMMARY OF THE INVENTION

It is one object of the present invention to provide novel polymer compositions useful for the manufacture of surgical devices.

It is another object of this invention to provide polymer compositions which are comprised of novel blends of two or more polymers.

It is still another object of the present invention to provide absorbable surgical devices having improved mechanical properties which are manufactured from the novel polymer compositions of the invention.

These and other objects are accomplished herein by providing an absorbable polymeric composition, suitable for the manufacture of surgical devices, comprising a blend of:

(a) polymer selected from the group consisting of glycolide homopolymer, lactide homopolymer, a mixture of glycolide homopolymer and lactide homopolymer and glycolide/lactide copolymer; and (b) from about 1 weight percent to about 50 weight percent of a polymer selected from the group consisting of polycaprolactone homopolymer, polytrimethylene carbonate homopolymer, copolymers of caprolactone and lactide, copolymers of caprolactone and glycolide, copolymers of trimethylene carbonate and lactide, copolymers of trimethylene carbonate and glycolide, copolymers of caprolactone, glycolide and lactide, copolymers of trimethylene carbonate, glycolide and lactide and mixtures thereof, based on the total weight of the blend.

In particularly useful embodiments, the compositions comprise a blend of a) a glycolide/lactide copolymer and b) a lactide/trimethylene carbonate copolymer wherein the trimethylene carbonate content of the copolymer is at least about 70%, preferably about 80%. These compositions are suitable for forming absorbable fibers.

The term "blend" is used herein in its broadest sense and embraces all types of blends known to those skilled in the art, including physical and chemical blends.

Other objects of the invention are achieved herein by providing absorbable surgical devices derived from the afore-described polymer blend compositions of the present invention.

DETAILED DESCRIPTION OF THE INVENTION

Copending U.S. patent application Ser. No. 07/654,234 now abandoned filed on Feb. 12, 1991 discloses a bioabsorbable reinforced composite material and method for the production thereof, wherein a component of the composite material may comprise a blend of homopolymers or copolymers of glycolide and lactide and polycaprolactone, and/or polytrimethylene carbonate.

In accordance with the present invention, it has now been found that absorbable surgical devices manufactured from these blends comprised of glycolide homopolymer, lactide homopolymer, glycolide/lactide copolymer or mixtures thereof and polycaprolactone homopolymer, polytrimethylene carbonate homopolymer and/or copolymers of caprolactone or trimethylene carbonate and glycolide and/or lactide, wherein the caprolactone or the trimethylene carbonate is the predominant monomer, possess improved physical and mechanical properties in comparison with surgical devices derived from glycolide or lactide homopolymer or glycolide/lactide copolymer alone.

More particularly, surgical devices prepared from the polymer blends of the present invention comprising glycolide or lactide homopolymer or glycolide/lactide copolymer and polycaprolactone or polytrimethylene carbonate homopolymer and/or copolymers of caprolactone or trimethylene carbonate and glycolide and/or lactide, wherein the caprolactone or the trimethylene carbonate is the predominant monomer (i.e. greater than 50 mole percent preferably at least 80 mole percent), are found to exhibit improved impact resistance, improved crazing properties and improved cyclic flexibility, both when annealed and nonannealed.

The novel polymer compositions of the present invention are blends of at least two polymers one of which is polycaprolactone homopolymer or polytrimethylene carbonate homopolymer or copolymer of polycaprolactone and glycolide and/or lactide or copolymer of trimethylene carbonate and glycolide and/or lactide or a mixture thereof.

In particular, the novel blends of the present invention comprise polycaprolactone homopolymer or polytrimethylene carbonate homopolymer or copolymer of polycaprolactone and glycolide and/or lactide or copolymer of trimethylene carbonate and glycolide and/or lactide or mixtures thereof and a polymer selected from a glycolide homopolymer, a blend of a glycolide homopolymer and a lactide homopolymer, a glycolide/lactide copolymer or mixtures thereof.

For the glycolide homopolymer and lactide homopolymer or glycolide/lactide copolymer employed, the proportion of glycolide in relation to lactide in the composition can vary depending upon the physical properties desired. For example, if the proportion of lactide is too high, the absorption time of a surgical implant device derived therefrom may be too long and if the glycolide proportion is too high, the breaking strength (tensile strength) retention upon implantation in the body of the device may be unacceptable. Typically acceptable results are achieved when up to about 50% glycolide, in relation to the amount of lactide, is used. Thus, preferred copolymers useful in the practice of the present invention are those comprising about 18/82 glycolide/lactide (mole percent), 10/90 glycolide/lactide (mole percent) 35/65 glycolide/lactide (mole percent) and 42/58 glycolide/lactide (mole percent).

The glycolide homopolymers, lactide homopolymers and glycolide/lactide copolymers employed in the blends of the present invention are known materials and are readily synthesized by known methods. Generally, the glycolide and/or lactide homopolymer and glycolide/lactide copolymers employed in the blends of the present invention have a molecular weight such that they have an inherent viscosity of from about 0.9 to about 2.0 dl/g and preferably about 1.0 to about 1.8 dl/g measured at 30° C. at a concentration of 0.25 g/dl in chloroform or hexafluoroisopropanol (HFIP). Particularly preferred glycolide/lactide copolymer for the purposes of the present invention are the two-phase or multi-phase compositions disclosed in U.S. Pat. No. 4,744,365, the entire contents of which is incorporated by reference herein.

The polycaprolactone homopolymers and copolymers employed in polymer blends of the present invention are also well known and commercially available materials. For the purposes of the present invention, polycaprolactone homopolymers or copolymers having an inherent viscosity of from about 0.8 to about 2.5 dl/g measured at 30° C. and a concentration of 0.25 g/dl in chloroform or HFIP are generally employed.

The polytrimethylene carbonate homopolymers and copolymers used in the practice of the present invention are also well known and commercially available materials. For purposes of the present invention polytrimethylene carbonate homopolymers having an inherent viscosity of from about 0.8 to about 2.5 dl/g measured at 30° C. and a concentration of 0.25 g/dl in chloroform or HFIP are generally used.

Copolymerization of caprolactone or trimethylene carbonate with glycolide and/or lactide has been found to facilitate handling of the caprolactone or trimethylene carbonate, e.g., processing through and removal from extrusion equipment.

In particularly useful embodiments, the compositions of the present invention comprise a blend of: i) a copolymer of glycolide and lactide; and ii) a copolymer of lactide and trimethylene carbonate having a trimethylene carbonate content of at least about 70%, preferably about 80%. In these compositions, the glycolide/lactide copolymer preferably has a lactide content of greater than about 70% and may comprise between 70 and 80% of the blend. The lactide/trimethylene carbonate copolymer is preferably a random copolymer. These flexible, rubbery blend compositions have a longer absorption time compared to the same trimethylene carbonate copolymer alone; i.e., not blended with the glycolide/lactide copolymer.

The polymer blends of the present invention are typically prepared by melt blending the components of the blend. The glycolide and/or lactide homopolymer or mixture thereof or the glycolide/lactide copolymer is used in the blend in a major amount, that is, from about 50 to about 99 weight percent of the total weight of the blend, the remainder, i.e. from about 1 to about 50 weight percent, comprising polycaprolactone homopolymer and/or copolymer and/or polytrimethylene carbonate homopolymer and/or copolymer. Melt blending is typically carried out at a temperature of 170° C. to 200° C. for a time sufficient to liquify the components, the time being dependent on such parameters as vessel, heat transfer properties, and presence and extent of blending. Typically, melt time ranges from a few minutes for small amounts of polymer to a couple of hours for large quantities.

The polymer blends of the present invention can also be prepared as chemical blends. In situ polymerization techniques are particularly useful methods for forming the blend. For example, after polymerizing the first polymer component of the blend in a reactor, the monomers necessary to form the second polymer component are added directly to the same reactor with additional initiator. Polymerization of the second polymer component of the blend is carried out in the presence of the first polymer component of the blend, resulting in the formation of the desired blend.

It has also been found herein that surgical devices manufactured from the blends of the present invention possess the excellent afore-described physical properties whether or not annealed.

Whichever polymer blend of the present invention is used, the absorbable surgical devices are made, preferably, by injection molding the blend at temperatures in the range of from about 300° to about 400° F. at an injection molding pressure of, for example, about 1,500 psi. Typically, the feed for the injection molding apparatus is a melt blend of the two polymers in pellet form. The polymers should be quite dry when being injection molded in order to avoid hydrolytic degradation during processing. After molding, the surgical devices can be packaged and sterilized by conventional procedures. It may be desirable to anneal the devices to remove residual stresses and strains, to stabilize the shape of the device, and to reduce or eliminate defects in the piece. Annealing typically comprises reheating the polymeric device to above its glass transition temperature where chain mobility is greatest, and then slowly and gradually cooling the device to avoid reintroducing. Procedures, conditions and apparatus for annealing polymeric structures are well known in the art.

A wide variety of absorbable surgical devices can be manufactured from the polymer blends of the present invention. These include fasteners, such as staples, clips and the like and other implant devices, such as pins, bone screws, or the like.

As expressed hereinbefore, the surgical devices of the present invention exhibit excellent in vivo cyclic flex performance, a mechanical property which is highly desired in surgical devices and in particular, for example, in surgical implant devices, such as surgical fastener/retainer systems which, after implantation, are subject to a variety of forces and often undergo repeated flexing.

Furthermore, surgical devices manufactured from the novel polymer blends of the present invention exhibit improved impact resistance as well as improved crazing resistance. Crazing may be defined as surface cracking of the material as contrasted with impact resistance which is more a measure of a material's tendency to allow crack propagation. Crazing may be observed visually, such as for example, a polymeric article which is flexed will evidence crazing by fogging of an otherwise clear or transparent material. In surgical applications, once a surgical article crazes, although the article may continue to function for a limited period, the article may not exhibit the desired strength. Thus, a material with a more limited tendency to craze when fabricated, for example, into a surgical implant device such as a bone screw, would permit the bone screw to be torqued to a greater extent without a likelihood that the screw would craze and thereby become ineffective for its intended purpose.

The examples below are illustrative of the blends of the present invention and surgical devices derived therefrom.

EXAMPLE 1

A copolymer of glycolide and lactide is prepared as follows:

Hydroxyacetic acid (glycolic acid) is heated under nitrogen to 180° C. to remove impurities such as water. Pressure is then reduced and heating is continued for two hours to yield a prepolymer of polyglycolic acid, which is recovered and powdered.

The prepolymer is heated in the presence of $Sb_2O_3$ at 275° C. under low pressure with an argon purge and stirring. The prepolymer cracks and glycolide is distilled over and recovered in a cold vacuum receiver. Preferably, the glycolide is purified by conventional techniques, such as distillation, crystallization, and sublimation.

L-lactide is used alone or in combination with a small amount of the DL racemer. L-lactide is purified by crystallization from toluene solution. The DL racemer, if used, is purified by crystallization from ethyl acetate.

A mixture of the purified glycolide (18 mole percent) and lactide (82 mole percent) is charged to a reactor under an argon blanket. A solution of stannous octoate catalyst in diethyl ether is added to give 0.02% w. of catalyst, based on the total weight of glycolide and lactide. The reactor is further purged with argon and held at 5 psi while heating to 170°–175° C. Pressure and temperature are maintained for six hours.

The reaction product is isolated, comminuted, and treated to remove residual reactants. Any method capable of removing the unreacted monomers from the crude reaction product may be used. A preferred purification procedure is as follows.

After comminution, the crude reaction product is contacted with ethyl ether for about 72 hours in a Soxhlet-type extractor to remove unreacted monomer. Typically, 4–10% of the starting monomers remain unreacted, and the glass transition temperature of the crude copolymer is approximately 50° C. Removal of unreacted monomers raises the glass transition temperature. As will be understood by one skilled in the art, the composition of the copolymer may differ slightly from the composition of the starting monomeric mixture because the lactide and glycolide are not of equal reactivity.

After the extraction period, the partially purified copolymer is slowly heated under vacuum from ambient temperature to 140° C. over a period of about 48 hours. The slow rate of heating is desirable to prevent melting (strictly speaking, flowing together) of the co-polymer particles and to remove any water present. Desirably, dry inert gas is used to purge the system, and occasionally the heating step may require more than 48 hours to reach the desired glass transition temperature. The combination of slow heating and purging with dry gas removes any residual solvent (ethyl ether) present, thereby raising the glass transition temperature.

After removal of unreacted monomers (and of solvent, if solvent extraction is used), the purified copolymer is further dried if it was not dried enough in the monomer removal step and, in any event, stored to keep it dry.

Trimethylene carbonate is polymerized in a reactor at 160° C. with a stannous octoate catalyst. The polytrimethylene carbonate so formed is melt blended with the glycolide/lactide copolymer (18/82) described above in the reactor at a temperature of 190° C. and at a weight ratio of 25:75. The blended polymer is extruded, ground, extracted with ether, and dried in accordance with known procedures.

Surgical devices fabricated from this blended polymer exhibit excellent physical properties, including good impact resistance, resistance to crazing and cyclic flexibility.

EXAMPLE 2

A glycolide/lactide copolymer (18/82 mole ratio) prepared as described in Example 1 is melt blended with a polycaprolactone homopolymer at weight ratios of 85:15 and 80:20 in a reactor at a temperature of 190° C. The blended polymer is extruded, ground, extracted with ether, and dried, as are known in the art.

The melt blended polymers are injection molded at a temperature of 130° C. to 140° C. at an injection molding pressure, e.g., 1,500 to 1,750 psi, to form a series of test plates measuring 2.2 inch×2.7 inch×0.070 inch. One portion of the test plates are annealed at an annealing temperature of about 85° C. to 100° C. for 12 to 16 hours to remove internal stresses. A second portion of the test plates are not annealed. Control test plates are also injection molded from the glycolide/lactide copolymer described in Example 1, none of which are annealed.

EXAMPLE 3

The test plates injection molded as described in Example 2 are tested for impact resistance using a standard dart impact tester. The test plates are designated as follows:

Control: glycolide/lactide copolymer (18/82); unannealed

Sample 1: glycolide/lactide copolymer (18/82) blended with polycaprolactone at a weight ratio of 85:15; unannealed Sample 2: glycolide/lactide copolymer (18/82) blended with polycaprolactone at a weight ratio of 85:15; annealed Sample 3: glycolide/lactide copolymer (18/82) blended with polycaprolactone at a weight ratio of 80:20; unannealed Sample 4: glycolide/lactide copolymer (18/82) blended with polycaprolactone at a weight ratio of 80:20; annealed The results of the impact tests are set forth in the following Table I:

TABLE I

| Force (in-lb) | Control | Sample 1 | Sample 2 | Sample 3 | Sample 4 |
| --- | --- | --- | --- | --- | --- |
| 10 | 4 | 4 | 4 | 4 | 3 |
| 20 | 6 | 4 | 4 | 4 | 3 |
| 30 |   |   | 6 |   |   |
| 40 |   |   |   | 5 | 4 |

Mode of Failure:

1. No effect;
2. Slight fractures;
3. Indentation with some crazing;
4. Cracks at point of contact;
5. Hole punched at point of contact;
6. Shattered.

These results show that the polymeric blends of the present invention exhibit improved impact resistance as compared to a non-blended control, i.e., a glycolide/lactide copolymer without added polycaprolactone. In addition, the test plates for Samples 1–4 exhibit improved resistance to crazing. Improved cyclic flex performance is also to be expected.

EXAMPLE 4

A two-phase polymeric composition comprising glycolide and lactide is prepared according to the procedure described in U.S. Pat. No. 4,744,365. A first monomer mixture of glycolide and lactide at a mole ratio of 10:90 is polymerized in the presence of a stannous octate catalyst until the polymerization is substantially complete. To this glycolide/lactide copolymer is added a second monomer mixture consisting of additional glycolide, such mixture being added in sufficient quantity that the final mole ratio of the two-phase polymeric composition is 35:65 glycolide to lactide. After the additional glycolide polymerizes with the glycolide/lactide copolymer, the two-phase polymer composition is ground, dried and ether extracted in accordance with known procedures.

Polycaprolactone is combined with the two-phase glycolide/lactide polymeric composition at mole ratios of 5:95 and 10:90, melt blended therewith at a temperature of 170° C. to 200° C. and the resulting blends are pelletized for subsequent use as described below.

The pellets of melt blended polymer are injection molded at a temperature of 130° C. to 140° C. at an injection molding pressure, e.g., 1,500 to 1,750 psi, to form a series of test plates measuring 2.2 inch×2.7 inch×0.070 inch. Control test plates are also injection molded from the two-phase glycolide/lactide polymeric compositions. One portion of the test plates are annealed at an annealing temperature of about 85° C. to 100° C. for 12 to 16 hours to remove internal stresses. A second portion of the test plates are not annealed.

The test plates are tested for impact resistance using a standard falling dart impact tester. The test plates are designated as follows:

Control 1: two-phase glycolide/lactide polymer (35/65); unannealed

Control 2: two-phase glycolide/lactide polymer (35/65); annealed

Sample 1: two-phase glycolide/lactide polymer (35/65) blended with polycaprolactone at a weight ratio of 95:5; unannealed Sample 2: two-phase glycolide/lactide polymer (35/65) blended with polycaprolactone at a weight ratio of 95:5; annealed Sample 3: two-phase glycolide/lactide polymer (35/65) blended with polycaprolactone at a weight ratio of 90:10; unannealed Sample 4: two-phase glycolide/lactide polymer (35/65) blended with polycaprolactone at a weight ratio of 90:10; annealed The results of the impact tests are set forth in the following Table II:

TABLE 11

| Force (in-lb) | Control 1 | Control 2 | Sample 1 | Sample 2 | Sample 3 | Sample 4 |
|---|---|---|---|---|---|---|
| 10 | 4, 5 | 4 | | | | |
| 20 | 5 | 4, 5 | 4 | 2, 4, 2 | 2 | 2 |
| 30 | | | 5 | | | |
| 40 | 5, 6 | 5, 6 | | 4 | 3 | 3 |
| 50 | 5, 6 | | | | | |
| 60 | 6 | 6 | | 4, 4 | 3 | 3 |
| 80 | | | | 4, 4 | 3 | 3, 3, 3 |

These results show that the polymeric blends of the present invention exhibit improved impact resistance as compared to non-blended controls, i.e., glycolide/lactide polymers without added polycaprolactone. In addition, the test plates for Samples 1–4 exhibit improved resistance to crazing. Improved cyclic flex performance is also to be expected.

EXAMPLE 5

A copolymer of L-lactide and trimethylene carbonate (30:70 mole ratio) was prepared by adding 653 grams of L-lactide and 1848 grams of trimethylene carbonate to a reaction vessel, drying the reactants for at least 12 hours at 60° C. and reacting in an $N_2$ atmosphere in the presence of a stannous octoate catalyst at 160° C. with stirring at about 7 RPM.

After 4.5 hours, 7500 grams of a glycolide/lactide copolymer (18/82 mole ratio) prepared as described in Example 1 and dried for at least 12 hours at 60° C. was added to the vessel containing the lactide-trimethylene carbonate copolymer at 190° C. After 1.5 hours, stirring at about 3 RPM was commenced for another 1.5 hours at 190° C. The resulting blend may be extruded into fibers and contains 75% by weight of the glycolide/lactide copolymer.

EXAMPLE 6

A copolymer of L-lactide and trimethylene carbonate (30:70 mole ratio) is prepared as in Example 5. Once polymerization is complete, glycolide and lactide (18:82 molar ratio, 7500 grams total) which have been previously dried and purified, are added to the reactor with 5 grams of glycolic acid as an initiator. Polymerization of the glycolide/lactide copolymer is achieved in the presence of the lactide-trimethylene carbonate copolymer by heating at 170° C. for 6 hrs with stirring. The resulting blend may be extruded into fibers and contains 75% by weight of the glycolide/lactide copolymer.

What is claimed is:

1. A method for preparing an absorbable polymer composition comprising:

preparing a first polymer, said first polymer being made at least in part of trimethylene carbonate or ε-caprolactone;

preparing a second polymer, said second polymer being made at least in part of glycolide or lactide, said second polymer being prepared by adding a monomer and initiator to a reactor containing said first polymer and polymerizing said second polymer in the presence of said first polymer, whereby a blend of said first and second polymers is formed.

2. A method as in claim 1 wherein said step of preparing a first polymer comprises adding a first monomer charge comprising trimethylene carbonate to a reaction vessel and polymerizing at an elevated temperature.

3. A method as in claim 2 wherein said first monomer charge further comprises one or more monomers selected from the group consisting of glycolide, lactide and caprolactone.

4. A method as in claim 2 wherein trimethylene carbonate is the predominant monomer in the first monomer charge.

5. A method as in claim 2 wherein trimethylene carbonate comprises at least about 70% by weight of the first monomer charge.

6. A method as in claim 5 wherein the first monomer charge comprises glycolide and lactide in a combined amount of up to about 30 percent by weight.

7. A method as in claim 5 wherein the first monomer charge comprises lactide in an amount up to about 20%.

8. A method as in claim 1 wherein the first polymer comprises from about 1 to about 50 weight percent of the total weight of the blend.

9. A method as in claim 1 wherein the first polymer comprises from about 5 to about 25 weight percent of the total weight of the blend.

10. A method as in claim 1 wherein said step of preparing a second polymer comprises adding a second monomer charge comprising one or more monomers selected from the group consisting of glycolide and lactide and further comprising caprolactone or trimethylene carbonate to a reaction vessel.

11. A method as in claim 10 wherein said second monomer charge comprises glycolide and lactide.

12. A method as in claim 10 wherein said second monomer charge comprises up to 50% by weight of glycolide.

13. A method as in claim 10 wherein said second monomer charge comprises up to about 20 mole percent of glycolide.

14. A method as in claim 1 wherein said step of preparing a first polymer comprises adding a first monomer charge comprising E-caprolactone to a reaction vessel and polymerizing at an elevated temperature.

15. A method as in claim 14 wherein said first monomer charge further comprises one or more monomers selected from the group consisting of glycolide and lactide.

16. A method as in claim 14 wherein E-caprolactone is the predominant monomer in the first monomer charge.

17. A method as in claim 14 wherein E-caprolactone comprises at least about 70% by weight of the first monomer charge.

18. A method as in claim 17 wherein said first monomer charge further comprises up to 30 percent by weight of one or more monomers selected from the group consisting of glycolide and lactide.

19. A method as in claim 14 wherein said first monomer charge consists essentially of E-caprolactone.

20. A method as in claim 14 wherein said first polymer comprises up to about 25 weight percent of the total weight of the blend.

* * * * *